United States Patent [19]

Branemark

[11] Patent Number: 5,324,199
[45] Date of Patent: Jun. 28, 1994

[54] FIXTURE FOR ANCHORING IN BONE TISSUE

[75] Inventor: Per-Ingvar Branemark, Mölndal, Sweden

[73] Assignee: Medevelop AB, Mölndal, Sweden

[21] Appl. No.: 859,352

[22] PCT Filed: May 16, 1991

[86] PCT No.: PCT/SE91/00348
§ 371 Date: May 21, 1992
§ 102(e) Date: May 21, 1992

[87] PCT Pub. No.: WO91/18556
PCT Pub. Date: Dec. 12, 1991

[30] Foreign Application Priority Data

May 25, 1990 [SE] Sweden ............................... 9001885

[51] Int. Cl.$^5$ ............................................. A61C 8/00
[52] U.S. Cl. .................................... 433/174; 433/173
[58] Field of Search ................................ 433/174, 173

[56] References Cited

U.S. PATENT DOCUMENTS

| | | | |
|---|---|---|---|
| 3,499,222 | 3/1970 | Linkow et al. | 433/174 |
| 4,027,392 | 6/1977 | Sawyer et al. | 433/173 |
| 4,468,200 | 8/1984 | Münch | 433/174 |
| 4,872,839 | 10/1989 | Brajnovic | 433/173 |

FOREIGN PATENT DOCUMENTS

| | | | |
|---|---|---|---|
| 2662597 | 12/1991 | France | 433/174 |
| 2063680 | 6/1981 | United Kingdom | 433/174 |

*Primary Examiner*—Gene Mancene
*Assistant Examiner*—Cindy A. Cherichetti
*Attorney, Agent, or Firm*—Ostrolenk, Faber, Gerb & Soffen

[57] ABSTRACT

A fixture intended to be implanted into bone tissue, for example, the bone tissue of a jaw, for anchoring a prothesis, such as a tooth crown. The fixture includes a cylindrical head disposed on the end of a shaft for positionally fixing the prothesis. An upper and lower external thread section is formed on the shaft. The lower external thread section is screwed into a previously prepared hole in the bone tissue, the hole having a diameter that is substantially equal to a core diameter of the shaft. A thread-free zone is located along a mid-section of the shaft. The thread-free zone has a smooth outer surface to avoid the irritation of nerves present in the bone tissue in the vicinity of the fixture. Gently curving transitional portions connect the thread-free zone with the upper and lower external thread sections. The thread-free mid-section and the lower external thread section are provided with a coating of tissue friendly material.

6 Claims, 1 Drawing Sheet

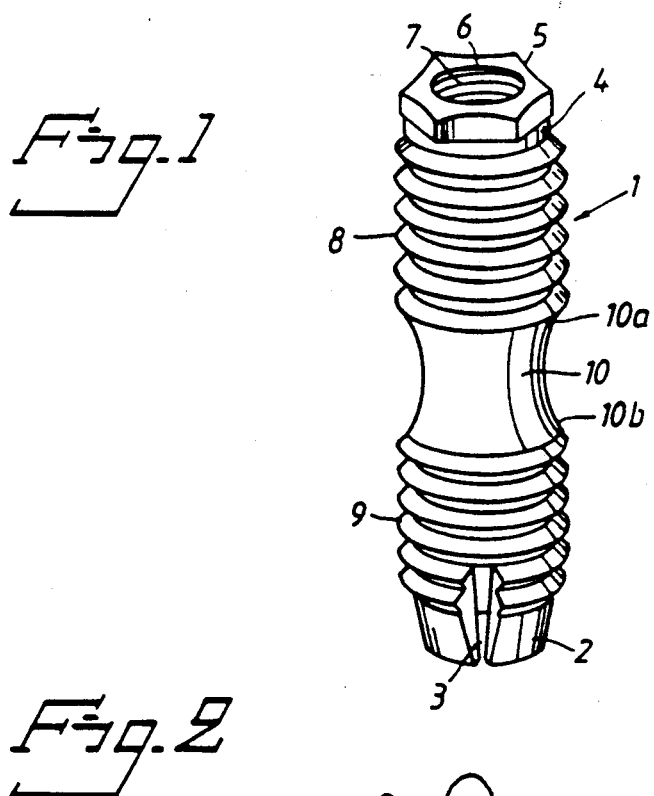
Fig.1
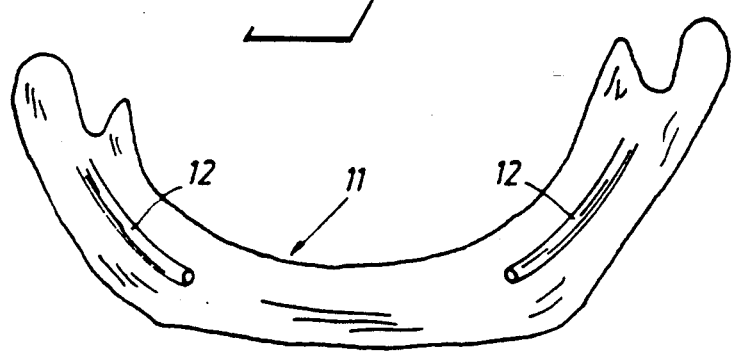
Fig.2
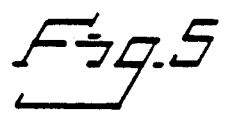
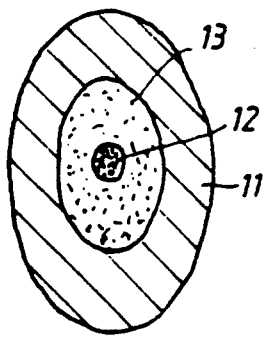
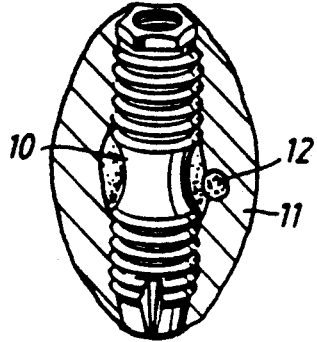
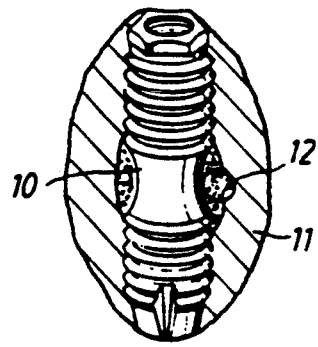

FIXTURE FOR ANCHORING IN BONE TISSUE

BACKGROUND OF THE INVENTION

The invention relates to a fixture intended to be implanted or anchored in bone tissue such as the bone tissue of the jaw, in order to support a prosthesis such as a tooth crown or the like. The fixture is provided with a surface coating of tissue-friendly material, at least in the area intended to contact the bone tissue, and has a cylindrical shaft provided with external threading and a cylindrical head. The fixture is arranged to be screwed into a previously prepared hole in the bone tissue, the diameter of the hole being substantially in equal to the core diameter of the shaft section.

A number of factors must be taken into consideration when implanting fixtures in the form of screws into bone tissue such as in the jaw-bone. When attaching a superstructure such as a dental prosthesis or the like. A primary factor is of course that integration of the fixture should occur as favourably as possible with minimum risk of infection and mechanical damage in the implantation region. Furthermore, it should be possible for the fixture to be fitted relatively quickly and simply, permitting rapid integration. Furthermore, the fixture and bandage should naturally be such as to minimize the risk of disturbance during the integration period.

One known technique, for instance, is to use a fixture comprising a cylindrically threaded shaft with a cylindrical head, the height of which is a fraction of the shaft diameter, and the diameter of which is slightly greater than the shaft diameter, with a short and gently curved transition being arranged between shaft and head. The head may be provided with a central axial hole and may be provided at its free end with formations facilitating assembly of a superstructure, for instance in the form of a crown or a base for a crown or the like.

During installation a hole is prepared in the jaw-bone, the bore diameter corresponding substantially to the core diameter of the shaft. The bore may be formed on or in the fixture itself, for instance at the lower end of the shaft. The threaded shaft of the fixture may suitably be arranged to cut the a thread in the jaw-bone for the shaft threading.

The technique described above has been used with success for many years. However, in recent years symptoms have been observed in certain cases, particularly when such fixtures are applied in the lower jaw, entailing motoric and/or sensory loss of feeling, often in the area of the lower lip. After thorough studies of these cases it has been established that the loss of feeling is caused by a nerve—the nervus alveolaris interior—located in the mandible coming into contact with the external threading of the implanted fixture. This probably causes irritation of the nerve, thereby disturbing the distal area supplied by the nerve.

It has now proved possible to eliminate these disturbances by means of the fixture proposed according to the present invention, the primary characteristic of which is that the threaded shaft section of the fixture has at least one zone without threading.

SUMMARY OF THE INVENTION

According to the invention this thread-free zone is arranged in the mid-section of the external thread so that it will be located within the marrow cavity of the jaw-bone after installation.

When the fixture according to the invention is installed by being screwed into the jaw-bone, the nerve is lifted out of the way and is subsequently replaced, i.e. when the fixture has been finally installed, against the thread-free zone of the fixture.

According to a suitable embodiment of the invention the thread-free zone has a smooth outer surface, is suitably arranged in the mid-section of the external thread and covers at least two thread pitches in the external threading.

According to a suitable embodiment, the diameter of the thread-free zone substantially coincides with the core diameter of the shaft and is connected to respective threaded sections by gently curved portions. The invention will be described more fully in the following with reference to an embodiment shown in the accompanying drawings.

BRIEF DESCRIPTION OF THE DRAWINGS

FIG. 1 shows a view in perspective of a fixture according to the invention,

FIG. 2 shows a diagrammatic sketch of a mandible, of a human jaw

FIG. 3 shows a section through the mandible shown in FIG. 2,

FIGS. 4 and 5 show the same section as FIG. 3 with the fixture inplace in the mandible.

DESCRIPTION OF THE PREFERRED EMBODIMENT

The fixture shown in FIG. 1 is generally shaped as a screw. The fixture 1 comprises an insertion end 2, suitably provided with slits 3 running axially upwards and having cutting edges to enable the screw itself to cut a thread in the bone tissue. The fixture comprises a neck portion 4 and a head 5. The head 5 has a central hole 6 with internal threading 7 for attachment of a superstructure such as a crown or the like, which is then fitted in bore 6 when the fixture 1 has become integrated into the bone tissue. The fixture 1 is also provided with a threaded shaft section comprising an upper, external thread 8 adjoining the head 5, and a lower external thread 9. Between the upper and lower external threads 8 and 9 is a thread-free zone 10, the diameter of which is substantially equal to the core diameter of the shaft. The thread-free zone 10 is joined to the upper thread 8 and the lower thread 9 by gently curved portions 10a and 10b, respectively.

FIG. 2 shows a diagrammatic sketch of a mandible 11 including nerves 12. From the section through the mandible shown in FIG. 3 it can be seen that the nerve 12, in this particular case the nervus alveolaris interior, is normally located in the marrow cavity 13 of the mandible 11.

When the fixture according to the invention is installed by being screwed into the jaw-bone, the nerve 12 is lifted out of the way during insertion see FIG. 4-and is subsequently replaced, as shown in FIG. 5, against the thread-free zone 10 of the fixture which has a substantially smooth and uniform outer surface. The previously observed irritation of the nerve is thus avoided since the nerve is no longer in contact with the threaded part of the fixture. Irritation of the nerve and the resulting drawbacks are thus avoided.

To install the fixture 1 a hole is suitably prepared in the bone tissue with a diameter substantially corresponding to the core diameter of the shaft. The fixture 1 is then screwed into this hole, cutting a groove for its external thread, preferably to a depth illustrated in FIGS. 4 and 5. During installation of the fixture the nerve is thus lifted out of the way and is then replaced against the thread-free smooth zone 10 of the shaft after completed installation is completed. The fixture then becomes integrated into the bone tissue over a suitable period of time and once osseo-integration has been achieved the proposed superstructure can be fitted on the fixture in known manner.

The invention has been described with reference to a fixture for carrying a dental prosthesis. However, it can of course also be used for anchoring other types of prostheses in bone tissue where it is feared that nerve irritation may occur against the external thread.

The thread-free zone 10 shown in the drawings may of course be different from that shown, i.e. it may have less extension in the longitudinal direction of the screw. However, it is important that there are a number of thread pitches on each side of the thread-free zone, and the thread-free zone should suitably be located approximately mid-way along the fixture in order to ensure that the fixture is located in the marrow cavity after installation.

Several thread-free zones may of course also be arranged along the threaded portion of the shaft. The fixture may suitably be manufactured of titanium and the shaft thread is suitably M 3.75.

Although the present invention has been described in relation to a particular embodiment thereof, many other variations and modifications and other uses will be apparent to those skilled in the art. It is preferred, therefore, that the present invention be limited not by the specific disclosure herein, but only by the appended claims.

I claim:

1. A fixture for implantation in bone tissue of a jaw, for anchoring a prothesis, comprising:
   a cylindrical shaft;
   a head disposed on said shaft for positional fixing the prothesis after implantation of the fixture into the bone tissue;
   an upper and lower external thread section formed on said shaft, said upper and lower external thread sections being arranged to be screwed into a previously prepared hole in the bone tissue, the hole having a diameter substantially equal to a core diameter of the shaft;
   a mid-section located on said shaft between said upper and lower external thread sections;
   a thread-free zone located along said mid-section of said shaft so as to be disposed within a bone marrow cavity of the jaw upon insertion of said fixture into said previously prepared hole, said thread-free zone having a smooth outer surface to avoid irritation of nervus alveolaris inferior present in the bone marrow cavity in the vicinity of the fixture; and
   gently curving transitional portions connecting said thread-free zone with said upper and lower external thread sections, wherein at least the thread-free mid-section and the lower external thread section are provided with a coating of tissue friendly material.

2. A fixture as claimed in claim 1, wherein the thread-free zone extends in the longitudinal direction of the shaft and covers at least two thread pitches in the external threading.

3. A fixture as claimed in claim 1, wherein the diameter of the thread-free zone substantially equals the core diameter of the shaft.

4. A fixture as claimed in claim 1, further comprising an open end disposed on the lower edge and provided with cutting edges in the form of longitudinal slits.

5. A fixture as claimed in claim 1, wherein said upper and lower external thread sections have a constant pitch and depth.

6. A fixture for implantation in bone tissue of a jaw, for anchoring a prothesis, comprising:
   a cylindrical shaft;
   a head disposed on said shaft for positional fixing the prothesis after implantation of the fixture into the bone tissue;
   an upper and lower external thread section formed on said shaft, said upper and lower external thread sections being arranged to be screwed into a previously prepared hole in the bone tissue, the hole having a diameter substantially equal to a core diameter of the shaft;
   a mid-section located on said shaft between said upper and lower external thread sections;
   a thread-free zone located along said mid-section of said shaft disposed within a bone marrow cavity of the jaw upon insertion of said fixture into said previously prepared hole, such that nervus alveolaris inferior present in the bone marrow cavity rests against said thread-free zone, said thread-free zone having a smooth outer surface to avoid irritation of the nervus alveolaris inferior in the vicinity of the fixture; and
   gently curving transitional portions connecting said thread-free zone with said upper and lower external thread sections, wherein at least the thread-free mid-section and the lower external thread section are provided with a coating of tissue friendly material.

* * * * *